Figure 1:
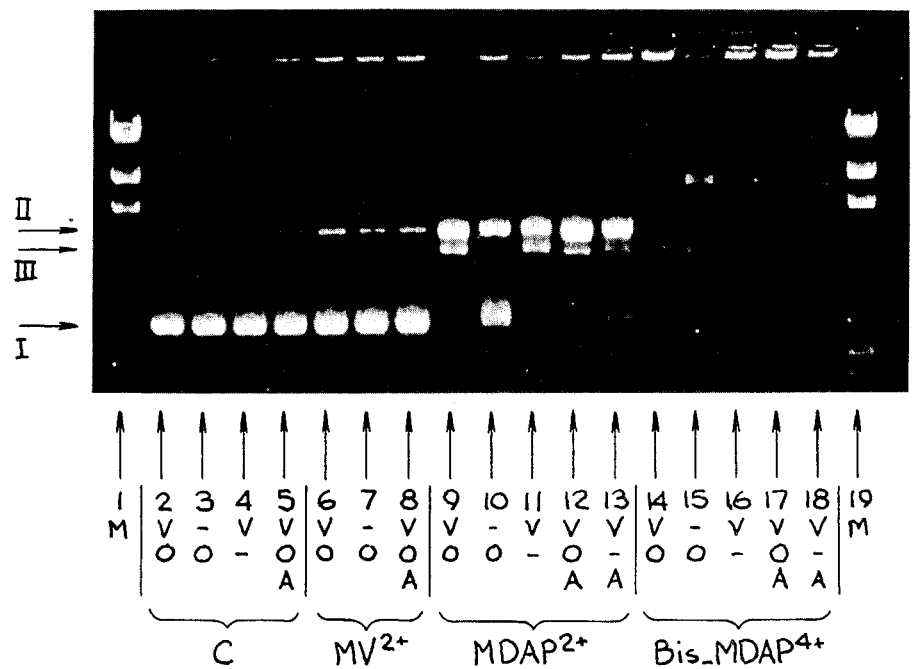

United States Patent [19]

Lehn et al.

[11] Patent Number: 4,925,937

[45] Date of Patent: May 15, 1990

[54] DIAZAPYRENE COMPOUNDS USEFUL FOR PHOTOCLEAVAGE OF NUCLEIC ACIDS

[75] Inventors: Jean M. Lehn; Jaroslaw Jazwinski; John Blacker, all of Strasbourg, France

[73] Assignee: Compagnie Oris Industrie, Paris, France

[21] Appl. No.: 141,607

[22] PCT Filed: Apr. 29, 1987

[86] PCT No.: PCT/FR87/00142

§ 371 Date: Dec. 15, 1987

§ 102(e) Date: Dec. 15, 1987

[87] PCT Pub. No.: WO87/06584

PCT Pub. Date: Nov. 5, 1987

[30] Foreign Application Priority Data

Apr. 29, 1986 [FR] France ................. 86 06212

[51] Int. Cl.$^5$ ................. C07D 401/14; C07D 471/22; C07H 21/00
[52] U.S. Cl. ........................ 540/477; 546/66
[58] Field of Search ............ 546/66; 540/477

[56] References Cited

U.S. PATENT DOCUMENTS 3,652,149  3/1972  Rogers .................. 546/66
3,853,589  12/1974 Andrews ................ 546/13

FOREIGN PATENT DOCUMENTS 249841  12/1987  European Pat. Off. ......... 546/66

OTHER PUBLICATIONS

K. A. Reich et al., Cleavage of DNA by the 1,10-Phenanthroline-Copper Ion Complex, Superoxide Mediates the Reaction Dependent on NADH and Hydrogen Peroxide, Journal of the American Chemical Society, vol. 103, 1981, pp. 3582-3584.
Chemical Abstracts, vol. 75, 1971, Abstract 157073(x), Radiation-Sensitive Materials Containing Nitrogenous Cationic Compounds, Mar. 30, 1971.
Hunig et al., Angew. Chem., 1980, No. 19 (1968), p. 799.
Hertzberg et al., JACS, 1982, 104, 313-315.
Huenig et al., Chem. Abst. 69-7840g (1968).
Jenny et al., Chem. Abst. 69-77134d (1968).
Lier et al., Chem. Abst. 70-11594t (1969).
Fischer et al., Chem. Abst. 85-182867y (1976).
Andrews, Chem. Abst. 86-141186c (1977).
Thulstrup et al., Chem. Abst. 87-167331s (1977).
Blacker et al., Chem. Abst. 105-221782v (1986).
Blacker et al., Chem. Abst. 107-235809n (1987).
Lehn, Chem. Abst. 108-85088f (1988).

*Primary Examiner*—Cecilia Shen
*Attorney, Agent, or Firm*—Bryan, Cave, McPheeters & McRoberts

[57] ABSTRACT

The present invention relates to a process for the photocleavage of nucleic acids which consists in bringing a nucleic acid into contact with a solution of a 2,7-diazapyrene derivative and in subjecting the resulting reaction mixture to irradiation with visible light.

7 Claims, 2 Drawing Sheets

DIAZAPYRENE COMPOUNDS USEFUL FOR PHOTOCLEAVAGE OF NUCLEIC ACIDS

The present invention relates to a process for the photocleavage of nucleic acids by 2,7-diazapyrenium dications, $DAP^{2+}$, or their dimeric species, bis-$DAP^{4+}$.

It also relates to novel diazapyrene derivatives; these are salts which release dications, $DAP^{2+}$, or tetracations, bis-$DAP^{4+}$, in solution.

Finally, 2,7-diazapyrenium dications coupled with oligonucleotides can form photoexcision reagents specific for nucleic acids.

Much research has been undertaken in recent years to find artificial reagents capable of cleaving nucleic acids and more particularly deoxyribonucleic acid and ribonucleic acid, commonly called DNA and RNA.

The majority of studies have been carried out with metal complexes which cleave DNA by an oxygen-dependent redox process or by photoactivation. Dyes of the acridine type have also been used to photodamage DNA.

Among the metal complexes which have been used, compounds carrying EDTA-Fe(II) groups and 1,10-phenanthroline-copper complexes may be mentioned in particular.

For example, in FEBS LETTERS, vol. 172, no. 1, Jun. 1984, BOUTORIN et al. describe reagents carrying EDTA-Fe(II) groups which are suitable for the direct cleavage of single-stranded nucleic acids.

Likewise, in SCIENCE, vol. 230, 1985, p. 679–681, TULLIUS et al. use EDTA-Fe(II) to cleave DNA.

HERTZBERG et al. [J. Am. Chem. Soc. 1982, 104, p. 313–315] recommend the use of (methidiumpropyl-EDTA)-Fe(II) as a cofactor in the cleavage of DNA for a number of antitumoral antibiotics.

The use of the 1,10-phenanthroline-copper complex to cleave DNA is described especially by REICH et al. in J. Am. Chem. Soc., Vol. 103, no. 12, 1981 and by R. FAGGIANI et al. in J. Am. Chem. Soc., Vol. 102, p. 5419–5421, 1980.

Moreover, it is known that dyes of the acridine type damage DNA. For example, FREIFELDER et al. [Biophysical Journal, Vol. 1, 1961] showed that DNA irradiated with visible light in the presence of acridine orange depolymerizes and undergoes cleavage.

It will be noted, furthermore, that 4,4'-bipyridinium ions, and in particular methylviologen, have been used in various redox and photoredox processes [AMOUYAL et al., Israel Journal of Chemistry 22, 1982, p. 117–123]. These processes can only take place in the presence of a photosensitizer or under ultraviolet irradiation.

Methylviologen, i.e. 1,1'-dimethyl-4,4'-bipyridinium chloride, commonly called $MV^{2+}$, can damage DNA under these conditions.

It has now been found that diazapyrene derivatives, and more particularly 2,7-diazapyrenium cations, can be used for the photocleavage of nucleic acids in visible light without the need for photosensitizers.

Thus, the present invention relates to a process for the photocleavage of nucleic acids which consists in bringing a nucleic acid into contact with a solution of a 2,7-diazapyrene derivative of the type defined below, and in subjecting the resulting reaction mixture to irradiation with visible light.

The diazapyrene derivatives which are suitable for the purposes of the invention correspond to formula (I) below:

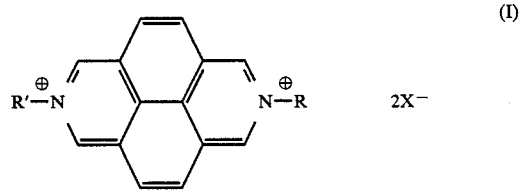

in which:
R and R', which are identical or different, represent: hydrogen; or
a linear or branched, saturated or unsaturated aliphatic hydrocarbon radical optionally interrupted by one or more heteroatoms such as, for example, oxygen, sulfur or nitrogen, it also being possible for the said hydrocarbon radical optionally to be substituted by hydroxyl, amino or thio groups, by an aryl group or by a heterocyclic group; or
R and R' are identical and represent a group of the formula $R_1Y^-$, in which $R_1$ is the group $-(CH_2)_3-$ and $Y^-$ is the sulfonato ion, $SO_3^-$; or a group of the formula:

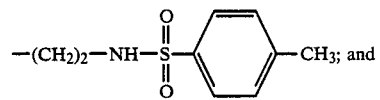

$X^-$ is either an anion or nothing if at least one of the substituents R and R' is of the formula $R_1Y^-$, in which case the derivatives are internal salts.

In the present description, the expression "aliphatic hydrocarbon radical optionally interrupted by one or more heteroatoms" also denotes aliphatic hydrocarbon groups containing the corresponding onium cations, in particular aliphatic hydrocarbon groups containing one or more quaternized nitrogen atoms, and especially the group of the formula:

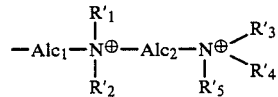

in which $Alc_1$ and $Alc_2$ are identical or different alkylene groups containing, for example, from 1 to 10 carbon atoms; $R'_1$ and $R'_2$, which are identical or different, are hydrogen or a lower alkyl group containing from 1 to 6 carbon atoms; and $R'_3$, $R'_4$ and $R'_5$, which are identical or different, are hydrogen or a saturated or unsaturated aliphatic hydrocarbon group, preferably an alkyl group containing 1 to 25 carbon atoms.

The compounds of formula I above in which R and R' are identical and represent hydrogen or a methyl group are known compounds which have been described by Hunig et al. [Angew. Chem. 1980, No. 19 (1968)].

It is also possible, in the process of the invention, to use the bis-diazapyrene derivatives corresponding to general formula (II):

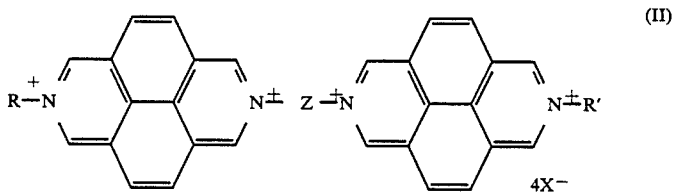
(II)

in which:

R, R' and X are as defined above and (Z) is a divalent radical which represents a saturated or unsaturated linear or branched aliphatic hydrocarbon chain optionally interrupted by one or more heteroatoms and/or optionally interrupted by one or more divalent aromatic or heterocyclic groups.

The hydrocarbon chains which form the radical (Z) can contain 2 or more carbon atoms and be interrupted by one or more heteroatoms selected from oxygen, sulfur and nitrogen atoms.

Preferred examples of divalent radicals (Z) are the radicals of formulae III to V below:

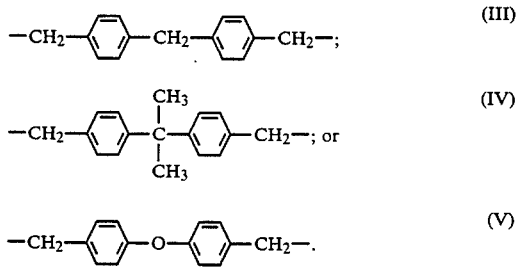

In formulae (I) and (II) above, the aliphatic hydrocarbon radicals preferably have 1 to 10 carbon atoms. Linear or branched alkyl groups having 1 to 6 carbon atoms are particularly preferred.

It is also possible, in the process according to the invention, to use the diazapyrene macrocycles corresponding to general formula (III):

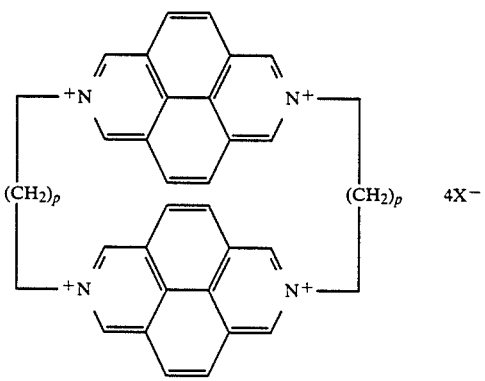

in which p is an integer between 1 and 15 and preferably equal to 8.

The diazapyrene derivatives of formulae (I) and (II) can all be obtained from 2,7-diazapyrene, or DAP, by one of the processes below. For convenience, the diazapyrene derivatives of formula (I) and those of formula (II) will be denoted in the remainder of the present description by the expressions "DAP$^{2+}$ derivatives" and "bis-DAP$^{4+}$ derivatives" respectively.

Synthesis of the DAP$^{2+}$ derivatives

Process A

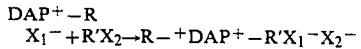

$X_1$ and $X_2$, which are identical or different, have the same meaning as X.

This process comprises essentially two steps involving N-substitution of the DAP, by the radicals R and R' respectively, and the compound obtained can then optionally be converted, by ion exchange, to the corresponding compound in which $X_1$ and $X_2$ are identical. It will be noted that if R and R' are identical, the two substitution steps are performed simultaneously. These steps are carried out in an appropriate solvent, for example dimethylformamide (DMF), chloroform or acetonitrile. DMF is suitable if it is desired to effect the two substitutions simultaneously (for example R=R'=CH$_3$), the reaction being carried out at room temperature; otherwise, chloroform should be used for the first substitution step and acetonitrile for the second (R≠R'), in which case the first substitution step is advantageously carried out at room temperature and the second under reflux.

This process is especially suitable for the preparation of the DAP$^{2+}$ derivatives in which R and R' are an aliphatic hydrocarbon radical of the type defined above, and in particular for the preparation of N,N'-dimethyl-2,7-diazapyrenium dichloride, hereafter called MDAP$^{2+}$(Cl$^-$)$_2$, which is illustrated by the following scheme:

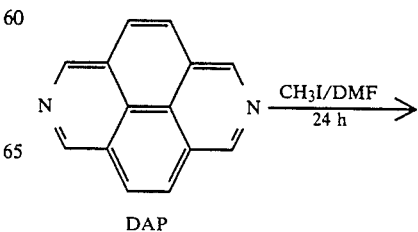
DAP

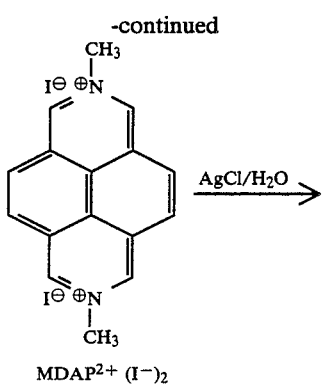

MDAP²⁺ (I⁻)₂

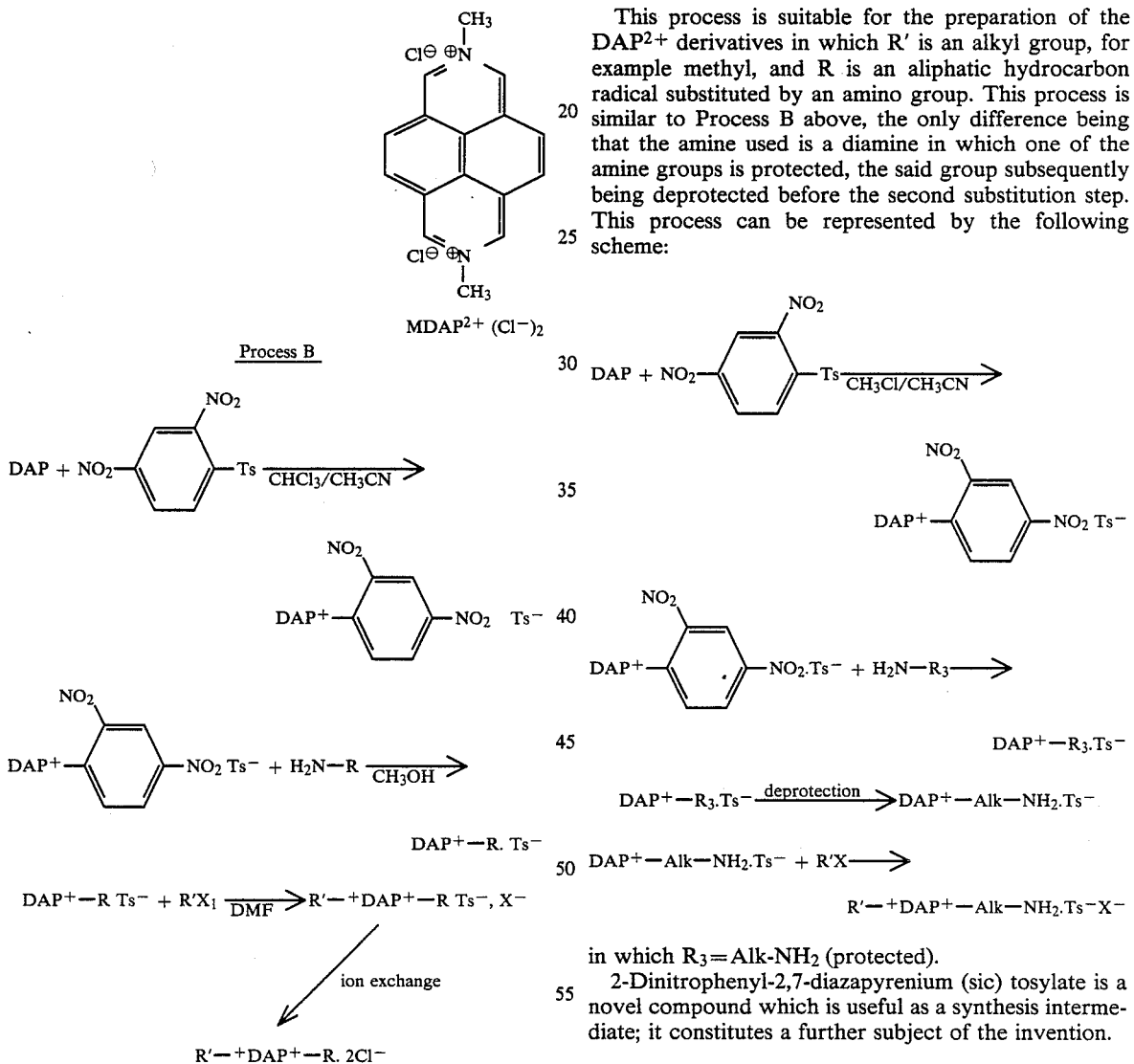

Process B in which Ts⁻ = anion, for example tosylate:

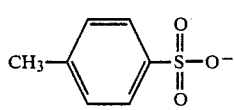

It will be noted that Ts⁻ can be replaced by another anion.

This process is suitable for the preparation of the DAP²⁺ derivatives in which the radical R is an aliphatic hydrocarbon radical substituted by a hydroxyl group, in particular a hydroxyalkyl group, and R' is an alkyl group, for example methyl. This process consists in first preparing a 2-dinitrophenyl-2,7-diazapyrenium (sic) salt, for example the tosylate, as a synthesis intermediate, by reacting DAP with a 2,4-dinitrophenyl salt such as the tosylate, in an appropriate solvent, for example a chloroform/methanol mixture under reflux, and then reacting this intermediate with an amine substituted by a radical R; the second step involves N-substitution with a halide of the formula R'X, as in Process A.

Process C

This process is suitable for the preparation of the DAP²⁺ derivatives in which R' is an alkyl group, for example methyl, and R is an aliphatic hydrocarbon radical substituted by an amino group. This process is similar to Process B above, the only difference being that the amine used is a diamine in which one of the amine groups is protected, the said group subsequently being deprotected before the second substitution step. This process can be represented by the following scheme:

in which R₃ = Alk-NH₂ (protected).

2-Dinitrophenyl-2,7-diazapyrenium (sic) tosylate is a novel compound which is useful as a synthesis intermediate; it constitutes a further subject of the invention.

Process D

This process is suitable for the preparation of the DAP²⁺ derivative in which R and R' are identical and represent a radical R₁Y⁻ of the type defined previously:

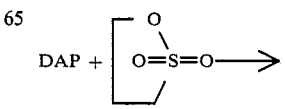

-continued

This process consists in reacting a partial solution of DAP in anhydrous acetone with propanesultone at the reflux temperature.

Process E

This process is suitable for the preparation of the DAP$^{2+}$ derivative in which R and R' are identical and represent the group of the formula:

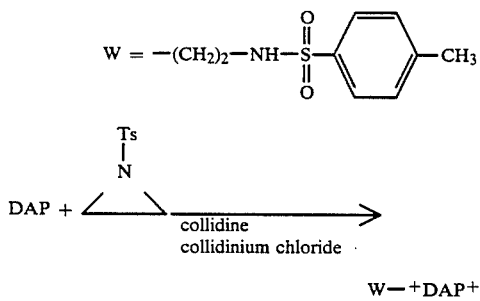

This process therefore consists in reacting DAP with aziridine in the presence of collidine and collidinium chloride.

Synthesis of the bis-DAP$^{4+}$ derivatives

The process for the preparation of these bis-DAP$^{4+}$ derivatives consists essentially in reacting two molecules of DAP with one molecule of a dihalide of the formula $X_1 - Z - X_1$, in which $X_1$, $X_2$ and $Z$ are as defined above, and then in effecting the N-substitution of the remaining nitrogens in the DAP molecules. Each step is advantageously carried out in acetonitrile at the reflux temperature.

This process can be represented by the following scheme:

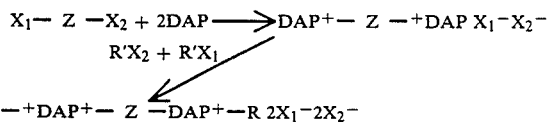

Synthesis of the bis-DAP$^{4+}$ macrocycles

The process for the preparation of the macrocycles of formula III, which are also called "bis-DAP$^{4+}$ macrocycles", consists in reacting naphthalene-1,4,5,8-tetracarboxylic anhydride of formula VI with a diamine of the formula $NH_2-(CH_2)_p-NH_2$ in dimethylformamide and in the presence of acetic acid. The macrocycle formed by this reaction is then reduced in the presence of lithium aluminum hydride and aluminum chloride to form the compound of formula VII, which is then converted to the compound of formula III. The first step of this process is a modified version of the process described by J. W. Verhoeven in Recueil Journal of the Royal Netherlands Chemical Society, 95/4, Apr. 1976, p. 89.

The second and third steps of this process are an adaptation of the process described by HUNIG et al., Ann. Chem. 1973, 339.

The reaction scheme of this process is as follows:

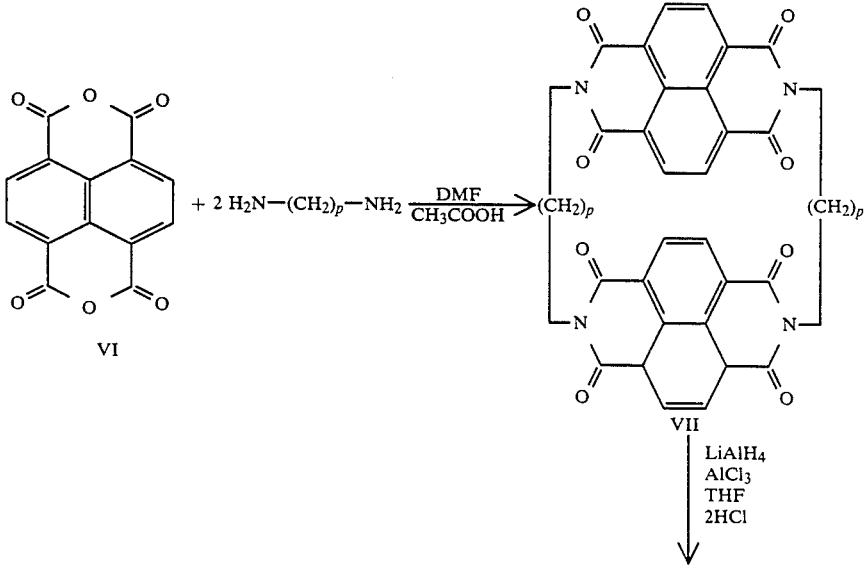

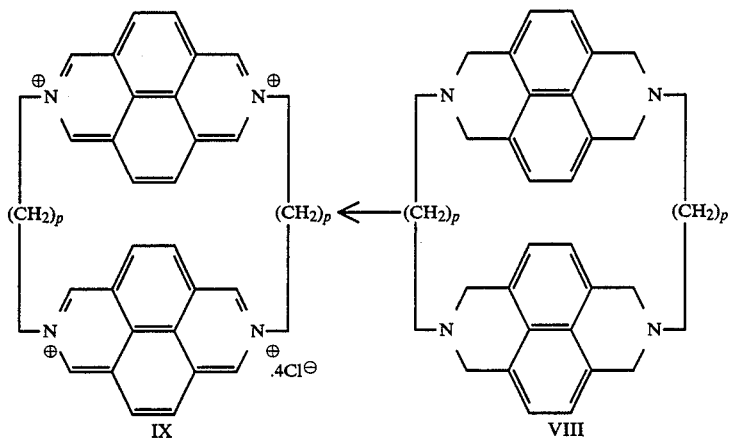

IX · 4Cl⊖   VIII

The diazapyrene derivatives according to the invention are fluorescent compounds.

The diazapyrene (DAP) used as the starting material in the above synthesis can be obtained from the commercially available naphthalene-1,4,5,8-tetracarboxylic anhydride of formula VI according to the following reaction scheme:

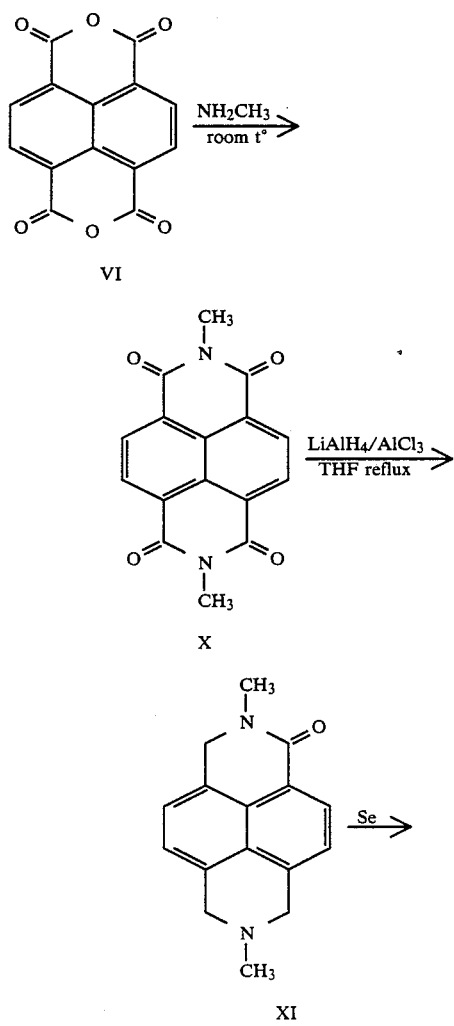

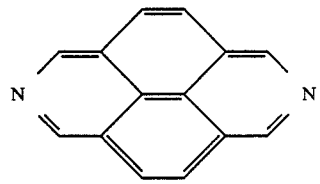

DAP

In an adaptation of the process of HUNIG et al., Angew. Chem. 180 (1968) no. 19, the naphthalene-1,4,6,8-tetracarboxylic (sic) anhydride of formula VI is first converted to the corresponding bis(N-methylimide) of formula X by reaction with methylamine at room temperature. The imide X is then treated with an LiAlH$_4$/AlCl$_3$ mixture in tetrahydrofuran under reflux to form the compound of formula XI, which is then reacted for about 4 hours, in the presence of selenium, at a temperature of between 265° and 300° C., to give DAP.

The compounds which are particularly appropriate for the purposes of the invention are:

(1) the compounds of formula (I) in which R and R' are a methyl group, or MDAP$^{2+}$ derivatives (sic);

(2) the compounds of formula (I) in which one of the substituents R or R' is a lower alkyl, for example methyl, and the other is an alkyl group substituted by a hydroxyl or thio group or an amino group, namely the groups of the formulae —(CH$_2$)$_n$—OH, —(CH$_2$)$_n$—SH or —(CH$_2$)$_n$—NH$_2$, in which n is preferably between 1 and 10; and (3) the compounds of formula (II) in which (Z) corresponds to one of formulae III to V and R and R' are a lower alkyl group, for example methyl.

The diazapyrene derivatives of formulae (I) or (II) containing one or two 2,7-diazapyrenium dications have a planar structure. By virtue of this planar structure, these compounds interact with the nucleotides of DNA or RNA in the same way as intercalating drugs such as actinomycin and bleomycin. Furthermore, under the action of irradiation with visible light, the derivatives according to the invention can cleave DNA or RNA into several strands.

It should be stated that the derivatives of formula (II), or bis-DAP$^{4+}$ derivatives, are more reactive than the derivatives of formula (I), or DAP$^{2+}$ derivatives, because two 2,7-diazapyrenium cations are present in their molecule. They also have a greater selectivity and a greater stability during photocleavage.

Furthermore, the derivatives of formula (I) in which one of the substituents R or R' is an aliphatic hydrocarbon radical substituted by a hydroxyl or amino group can be coupled by covalent bonding to an oligonucleotide or an oligodeoxynucleotide including a chain of natural nucleotides which may have been modified or synthesized.

This coupling can be effected by processes known to those skilled in the art. For example, it is possible to use the synthetic processes described in French Patent No. 83 01 223, which is cited in the present Application by way of reference. These processes consist inter alia in coupling the hydroxyl of the $DAP^{2+}$ derivative with an oligonucleotide 3'-phosphodiester or 5'-phosphodiester, with an oligonucleotide 3',5'-bis(phosphodiester) or with an oligodeoxynucleotide 2'-phosphodiester, the oligonucleotides or oligodeoxynucleotides being correctly protected. Thus, it is possible to obtain oligonucleotide (or oligodeoxynucleotide)/$DAP^{2+}$ or $DAP^{2+}$/oligonucleotide (or oligodeoxynucleotide)/$DAP^{2+}$ coupling products, which can constitute very selective photoexcision reagents.

The oligonucleotide or oligodeoxynucleotide chain of the coupling product can bind selectively to any complementary sequence. Through the presence of at least one 2,7-diazapyrenium dication in this coupling product, the DNA or RNA can easily be cleaved selectively at particular sites, the position of which is determined by the oligonucleotide which binds to the complementary sequence.

It will be noted that the oligonucleotide/$DAP^{2+}$ coupling product can subsequently be coupled with another reagent, which may be any kind of revealing agent, for example a marker such as, in particular, an acridine-type dye, or an intercalating agent, and can produce a dual-function coupling product, one of the functions being photocleavage and the other function being provided by the second reagent.

Photocleavage of DNA

The process of the invention will now be described with reference to $MDAP^{2+}$ or its dimeric species bis-$MDAP^{4+}$ simply for the sake of convenience and without thereby restricting it to these derivatives only.

Experiments carried out on DNA under the conditions indicated below showed that the dication $MDAP^{2+}$ or its dimeric species bis-$MDAP^{4+}$ cleave DNA under irradiation with visible light.

The experiments were performed by illumination for one hour with visible light (250 W slit projector fitted with a filter suitable for letting through only visible light of $\lambda > 395$ nm) of an aqueous solution containing double-stranded supercoiled circular DNA ($2.6 \cdot 10^{-8}$M) and the chloride of $MDAP^{2+}$ or bis-$MDAP^{4+}$ ($2.6 \cdot 10^{-4}$M) in tris buffer at pH 7.8 and at $3 \pm 1°$ C. The reaction was carried out in the presence or absence of air (oxygen) or EDTA.

The double-stranded supercoiled circular DNA, hereafter called scDNA, was prepared by the known procedures using E. coli bacteria infected with the plasmid pBR322, and subsequently purified by electro-elution so as to be virtually devoid of cut scDNA.

On incubation with the restriction enzyme ECOR1, the plasmid pBR322 gives a linear plasmid or double-stranded linear DNA, which was used as a marker in the electrophoretic analysis carried out after the above photocleavage experiment.

By way of comparison, the same experiment was performed using methylviologen, $MV^{2+}$, to replace the derivative of the invention. A solution of scDNA by itself, a solution of scDNA containing oxygen or a solution of scDNA containing oxygen and EDTA was also subjected to the same treatment (illumination with visible light under the above conditions) to serve as a control.

The results obtained are shown in the attached FIG. 1, which is a photograph of the gel after electrophoresis of the solutions in the various experiments, and are commented upon below. In this figure:

I denotes scDNA, II denotes cut scDNA and III denotes linear DNA;

the abbreviations used denote the following:

M = marker
C = control
V = visible light
O = oxygen
A = EDTA

Measurement of the optical density of each band gave the following proportions of the forms, I, II and III in %:

| Band no. | Form I | Form II | Form III |
|---|---|---|---|
| 2 | 93 | 7 | — |
| 6 | 82 | 18 | — |
| 7 | 88 | 12 | — |
| 8 | 86 | 14 | — |
| 9 | — | 73 | 27 |
| 10 | 53 | 47 | — |
| 11 | — | 68 | 32 |
| 12 | — | 77 | 23 |
| 13 | 16 | 72 | 12 |

(A) Experiments with $MDAP^{2+}$ (1) As shown by bands 9 to 13 in FIG. 1, $MDAP^{2+}$ efficiently cleaves scDNA under irradiation with visible light under the conditions used, giving mainly cut scDNA by cleavage of a single strand, but also linear DNA by cleavage of both strands when the reaction continues.

With lower concentrations of $MDAP^{2+}$, less cleavage takes place, the conversion to the cut scDNA form being almost complete at a concentration of $2 \cdot 10^{-5}$M and only slight at $2 \cdot 10^{-6}$M and below.

(2) It will be noted that there was no significant cleavage of the scDNA in the absence of light.

(3) Removal of the oxygen through degassing by freeze-thawing slightly reduces the efficiency of the photocleavage.

(4) The addition of EDTA does not affect the reaction in the presence of oxygen, but seems to reduce the reaction when it is carried out in the absence of oxygen.

(5) It will be noted that the migration of the scDNA is somewhat retarded by the photocleaving reagent used, suggesting that the latter intercalates in the scDNA.

(B) Experiments with bis-$MDAP^{4+}$ (1) Under the same conditions, bis-$MDAP^{4+}$ seems to be more efficient than $MDAP^{2+}$, giving small DNA fragments by multiple cleavage of both strands (bands 14 to 18).

(2) The cleavage reaction is so efficient that it becomes difficult to exclude light. It is nevertheless possible to observe that migration of the scDNA is appreciably retarded, indicating a strong and probably multiple interaction of the bis-MDAP$^{4+}$ with the plasmid pBR322.

(3) In view of the efficiency of the reaction, it is not possible to note any kind of oxygen or EDTA effect.

The effect of bis-MDAP$^{4+}$ decreases at lower concentrations, the cleavage still being complete at $10^{-5}$M but only slight at a lower concentration.

(C) Experiments with MV$^{2+}$ (bands 6 to 8) and control experiments (bands 2 to 5)

These experiments show that, under the same conditions, there is no cleavage or practically no cleavage with MV$^{2+}$. Furthermore, there is no reaction in the absence of photocleaving reagent.

As other experiments have shown that MDAP$^{2+}$ photo-oxidizes a variety of substrates under irradiation with visible light, one may consider, without however wishing to restrict oneself to any particular theory, that the cleavage reaction takes place via local photo-oxidation, at the site of interaction, by the excited state of the species MDAP$^{2+}$. The electron donor may be ribose, because it has been found that ribose itself photoreduces MDAP$^{2+}$.

The retarding effect of EDTA in the absence of oxygen would indicate that the oxidation of the external donor is competing with the oxidation of the internal donor.

The effect produced by removal of the oxygen, which is slight but not negligible, indicates that the cleavage reaction may also involve the reaction system, as with the photosensitive reduced metal complexes. The DAP$^{+}$ cation initially produced by photoreduction could then react with the oxygen to generate superoxide, as happens with MV$^{+}$ itself [Biochim. Biophys. Acta 1973, 314, 372].

Other experiments have been performed under the same conditions as above with proflavin, which is an acridine-type dye, and it has been found that proflavin is a comparable DNA photocleaving reagent to bis-MDAP$^{4+}$ and that, at a concentration of $2 \cdot 10^{-4}$M, it leads to extensive cleavage of DNA to give linear DNA. At lower concentrations ranging from $2 \cdot 10^{-6}$M to $2 \cdot 10^{-7}$M, the efficiency decreases.

The photocleavage process with proflavin is thought to involve photo-oxidation of the DNA, at the site of intercalation, with generation of a reduced dye. The acridine-type dyes are indeed well known for undergoing photoreduction with oxidation of the substrate.

Being flat molecules, the derivatives of the invention interact with the nucleotides in DNA or RNA in the same way as intercalating drugs such as actinomycin, bleomycin etc. It has been noted, moreover, that the fluorescence of the derivatives disappears when binding to the DNA takes place. It is therefore possible to follow the course of the photocleavage reaction by fluorescence.

Other experiments were carried out with single-stranded DNA, or ssDNA, and are reported below.

Solutions of MDAP$^{2+}$ and bis-MDAP$^{4+}$ at concentrations ranging up to $4 \cdot 10^{-4}$M were prepared with double-distilled water and adjusted to pH 7.6 with hydrochloric acid.

Circular scDNA and circular ssDNA were obtained from the plasmids pBR322 and M13mp19 respectively and purified by conventional electroelution processes.

The following were mixed carefully in glass test-tubes:
the diazapyrene derivative MDAP$^{2+}$ and bis-MDAP$^{4+}$
ssDNA or scDNA
Tris buffer pH 7.6
in appropriate amounts to give concentrations of diazapyrene derivatives of $5 \cdot 10^{-6}$M and $10^{-5}$M. Each tube was kept under a constant pressure of oxygen using known means and subjected to irradiation with visible light (250 W projector; $\lambda > 395$ nm) for $\frac{1}{2}$ hour, the tubes being kept at 3° C. in a bath of iced water.

Figure 2:
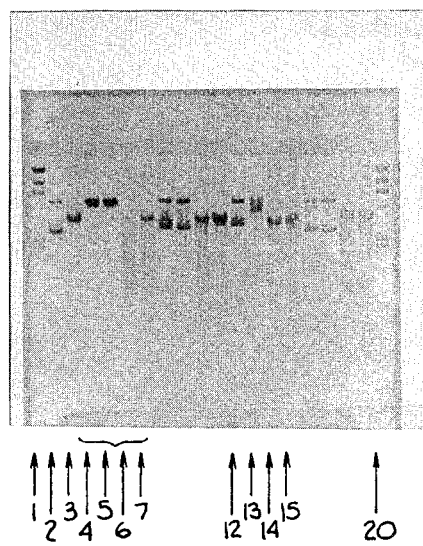

After irradiation, the tubes were kept in the dark and stored at 3° C. Samples from each tube were mixed with glycerol and subjected to electrophoresis on agarose gel (Sigma Type II EEO) (6 hours at 120 V and 80 mA). The agarose gel was stained with ethidium bromide and photographed. The attached FIG. 2 is a photograph of this gel, on which the bands correspond to the different experiments performed, the concentrations being indicated below.

| Band no. | DNA | Diazapyrene derivative | Concentration of the said derivative |
| --- | --- | --- | --- |
| 4 | scDNA | MDAP$^{2+}$ | $10^{-5}$ |
| 5 | " | " | $5 \cdot 10^{-6}$ |
| 6 | ssDNA | " | $10^{-5}$ |
| 7 | " | " | $5 \cdot 10^{-6}$ |
| 12 | scDNA | bis-MDAP$^{4+}$ | $10^{-5}$ |
| 13 | " | " | $5 \cdot 10^{-6}$ |
| 14 | ssDNA | " | $10^{-5}$ |
| 15 | " | " | $5 \cdot 10^{-6}$ |

Bands 1 and 20 correspond to the markers and bands 2 and 3 represent the scDNA and ssDNA subjected to irradiation in the absence of diazapyrene derivative; these DNAs were obtained in a known manner by reaction with the enzyme ECoR$_1$ and S$_1$ nuclease respectively.

This photograph shows that circular scDNA and ssDNA are cleaved in the presence of the diazapyrene derivatives of the invention.

It will be noted that the diazapyrene derivatives used in the process according to the invention retain their property of photocleaving DNA even when they are incorporated in micelles or liposomes. Micelles and liposomes may therefore be used as vehicles to carry the diazapyrene derivatives up to the DNAs to be cleaved.

The diazapyrene derivatives containing a long-chain hydrocarbon radical are particularly suitable for this type of use since the hydrocarbon radical allows better attachment to the liposome or micelle.

The invention will now be described in greater detail by the examples which follow.

EXAMPLE 1: Preparation of N-methyl-N'-benzyl-2,7-. . . (sic) dichloride

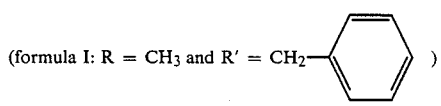

(formula I: R = CH$_3$ and R' = CH$_2$—)

1 g (0.0049 mol) of DAP was dissolved in 20 ml of chloroform. An excess of methyl iodide (3 ml; 0.048 mol) was then added. The reaction mixture obtained was stirred at room temperature for 24 hours. A yellow solid then precipitated. This yellow solid was separated from the reaction medium by filtration, washed with chloroform and dried in vacuo to give 1.61 g (0.0047 mol) of N-methyl-2,7-diazapyrene iodide (MDAP+I−) (yield: 96%).

Being partially protonated, this crude product was subjected to deprotonation by treatment with slightly alkaline water (pH∼7.8; water+traces of NH$_4$OH).

The crude product was then recrystallized from boiling methanol to give yellow crystals.

This product had the following physicochemical characteristics:

Elemental analysis: $C_{15}H_{11}N_2I.0.25H_2O$; MW=350.7;
Calculated: C 51.37; H 3.31; N 7.99;
Found: C 51.31; H 3.19; N 8.05;

$^1$H NMR spectrum (solvent D$_2$O/CF$_3$COOD; reference TMPS)

| |
|---|
| 10.05 ppm (s) |
| 10.03 ppm (s) |
| δ: 8.89 ppm (J = 9.19 Hz, AB, q) |
| 5.00 ppm (s) methyl |

The product obtained above (1 g; 0.0029 mol) was then suspended in 150 ml of anhydrous acetonitrile, and benzyl bromide (3 ml; 0.025 mol), filtered on a neutral Al$_2$O$_3$ column beforehand, was added. The resulting reaction mixture was refluxed for 12 hours, with stirring.

The yellow product obtained was filtered off, washed with chloroform and dried in vacuo.

Yield: 1.15 g (0.0022 mol), i.e. 77%.

The crude product thus obtained was stirred in the dark for 24 hours with water (100 ml) and silver chloride (obtained from 3 g of AgNO$_3$ and NaCl and correctly washed with water). The solid formed was filtered off and washed with hot water, the filtrate was then concentrated in vacuo and diluted with acetone (90 ml) and a yellow precipitate formed. This mixture was left overnight and the precipitate was filtered off and dried in vacuo.

Yield: 0.81 g (0.00213 mol), 73%.

The product obtained is N-methyl-N'-benzyl-2,7-diazapyrene dichloride, which has the following physicochemical characteristics:

Analysis $C_{22}H_{18}N_2Cl_2$; MW=381.3;
Calculated: C 69.29; H 4.72; N 7.35;
Found: C 69.07; H 4.89; N 7.38;

$^1$H NMR spectrum (solvent: D$_2$O; reference: TMPS)

| |
|---|
| 9.98 ppm (s) |
| 9.88 ppm (s) |
| 8.675 ppm (AB - q) |
| 7.41 ppm (m - benzyl) |
| 6.24 ppm (s) |
| 4.81 ppm (s, methyl) |

EXAMPLE 2: Preparation of the diazapyrene derivative bis-DAP$^{4+}$

| | |
|---|---|
| (formula II) | R = R' = CH$_3$ |
| | Z = —CH$_2$—C$_6$H$_4$CH$_2$—C$_6$H$_4$—CH$_2$— |

4,4-Bis(bromomethyl)diphenylmethane (0.174 g) was reacted with 2,7-diazapyrene (0.2 g) in anhydrous acetonitrile (15 ml) for 4 hours under reflux, with stirring. The yellow precipitate which formed was separated off by filtration, washed with chloroform and dried in vacuo.

Yield: 0.34 g; 85%

The crude product was recrystallized from hot water and analyzed. The product is of the formula:

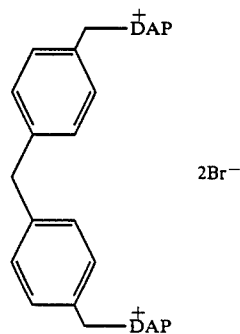

which has the following physicochemical characteristics:

Elemental analysis $C_{43}H_{30}N_4Br_2·3H_2O$, MW=816.6;
Calculated: C 63.24; H 4.44 N 6.86;
Found: C 63.17; H 4.25 N 6.65;

$^1$H NMR spectrum (solvent: D$_2$O/CF$_3$COOD; reference TMPS)

| |
|---|
| 10.09 ppm (s) |
| 10.00 ppm (s) |
| δ$_o$ = 8.81 ppm (J = 9.37 Hz, AB-q) |
| δ$_o$ = 7.91 ppm (J = 7.61 Hz, AB-q) |
| 6.29 ppm (s) |
| 3.98 ppm (s) |

This product (0.3 g) was suspended in 50 ml of acetonitrile and 0.5 ml of methyl iodide and refluxed for 4 hours, with stirring, to give a brownish-red solid insoluble in acetonitrile. This solid was filtered off, washed with chloroform and dried in vacuo.

Yield: 0.37 g; 90%.

Ion exchange was then carried out by suspending the resulting disalt (iodide/bromide) with silver chloride in water and stirring at room temperature for 24 hours. The solid formed was separated off by filtration and washed with hot water. The crude product (yellow solid, very soluble in water) was recrystallized several times from methanol or a methanol/ether mixture.

According to another procedure, the methylation step can be performed by mixing the product of the above formula with methyl bromide at 40°-50° C. in closed flasks for two to three days. This gives a water-soluble yellow product.

The product obtained in either case had the following physiochemical characteristics:

Elemental analysis: $C_{45}H_{36}N_4Cl_4·9H_2O$; MW=937;

Calculated: C 57.70; H 5.81; N 5.98;
Found: C 57.80; H 5.04; N 5.86;
¹H NMR spectrum (solvent: D₂O; reference TMPS)

| |
|---|
| 10.15 ppm (s) |
| 10.09 ppm (s) |
| 8.87 ppm (AB-q; J = 9.47 Hz) |
| 7.55 ppm (AB-q; J = 8.18 Hz) |
| 6.39 ppm (s) |
| 5.20 ppm (s) methyl |
| 4.13 ppm (s) |

EXAMPLE 3: Preparation of the bis-DAP⁴⁺ derivatives (formula II R = R' = CH₃;

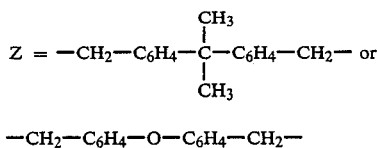

—CH₂—C₆H₄—O—C₆H₄—CH₂—

The procedure described in Example 2 was followed, the 4,4'-bis(bromomethyl)diphenylmethane being replaced by:
2,2'-[4,4'-bis(bromomethyl)diphenyl]propane (sic) and 4,4'-bis(bromomethyl)diphenyl ether to give respectively:
the compound of the formula:

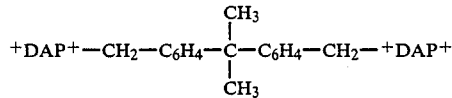

which has the following
NMR spectrum: 10.28 ppm (s); 10.21 ppm (s); 9.00 ppm (q-AB); 7.7 ppm (q-AB); 6.52 ppm (s); 5.14 ppm (s); 2.39 ppm (s) and the compound of the formula:

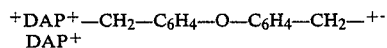

which has the following
NMR spectrum: 10.27 ppm (s); 10.18 ppm (s); 8.97 ppm (q-AB); 7.82 ppm (d); 7.34 ppm (d); 6.51 ppm (s); 5.10 ppm (s).

EXAMPLE 4: Preparation of 2,4-dinitrophenyl-2,7-diazapyrenium tosylate (synthesis intermediate)

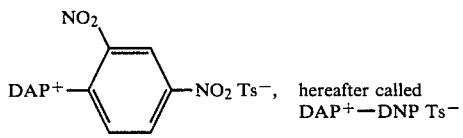

0.81 g (2.4·10⁻³ mol) of 2,4-dinitrophenyl tosylate (prepared by reacting tosyl chloride with 2,4-dinitrophenyl (sic)) and 0.49 g (4·10⁻³ mol) of 2,7-diazapyrene were refluxed in a mixture (50/50 v/v) of chloroform and acetonitrile.
The yellow precipitate formed was filtered off and redissolved in methanol; the new precipitate formed was washed in excess ether. The yellow precipitate obtained was then dried in vacuo.
Yield: 0.96 g, 73%
Melting point: 252°–254° C. (decomposition)
The elemental analysis of this product was as follows:
Calculated: C 59.78; H 3.34; N 10.33;
Found: C 59.82; H 3.10; N 10.41;
¹H NMR spectrum (solvent D₂O; reference TMPS)

| |
|---|
| 10.285 ppm (s) |
| 9.975 ppm (s) |
| 9.4 ppm (s) |
| 9.0 ppm (d,d J = 0.05 p) |
| 8.90 ppm (d, J = 0.05 p) |
| 8.675 ppm (d J = 0.05 p) |
| 8.5 ppm (d J = 0.05 p) |
| 7.575 ppm (d J = 0.041 p) |

EXAMPLE 5: Preparation of the diazapyrene derivative of formula I with R=H and R'=—(CH₂)₂—NH₂
The procedure of Process C was followed using the amine of the formula H₂N-(CH₂)₂NH₂ in which one amine group was protected by the carbobenzoxy group, C₆H₄—CH₂—O—CO—. 0.44 g of DAP⁺—DNP Ts⁻ was dissolved in 40 ml of anhydrous methanol and the solution obtained was placed in a dropping funnel.
The amine was separately prepared from the corresponding ammonium salt and dissolved (1.6·10⁻³ mol) in 20 ml of anhydrous methanol, with stirring. A few drops of collidine were then added to the reaction mixture, with continued stirring. The solution of DAP⁺—DNP Ts⁻ was then added dropwise over a period of one hour. The solution changed from deep red to brown. Stirring was continued for a further hour, after which the solvent was removed on a Büchner funnel. 300 ml of anhydrous ether were then added and a slightly brown precipitate formed. The solution was stirred further 1 h 30 minutes and filtered. The solid obtained was dried overnight in a desicator (sic).
Yield: 0.41 g; 94%.
The compound obtained has the following physico-chemical characteristics:
Elemental analysis MW=537
Calculated: C 64.53; H 5.94; N 7.51;
Found: C 64.58; H 5.00; N 7.32; NMR (ppm) 9.87 (s); 8.53 (d); 8.77 (d); 9.92 (s); 5.19 (t); 3.98 (t); 6.6 (s); 4.8 (s); 7.1 (s); 7.2 (d); 7.7 (d); 2.07 (s)
The amine group was then deprotected by reacting the product obtained with a mixture of acetic acid and hydrobromic acid at room temperature.
The product obtained corresponded to the formula ⁺DAP⁺—(CH₂)₂—NH₃⁺·3Br⁻, which has the following elemental analysis:
Calculated: C 39.19; H 3.28; N 8.57;
Found: 34.11; 3.22; 7.43;
The NMR spectrum (D₂O, TMPS) of this product showed peaks at 9.93 ppm, 8.80 ppm, 8.86 ppm, 10.09 ppm, 5.56 ppm and 4.00 ppm. The expected product is obtained by reacting a base with the resulting product.

EXAMPLE 6: Preparation of N-methyl-N'-hydroxypentyl-2,7-diazapyrenium dibromide (formula I: R=CH$_3$; R'=—(CH$_2$)$_5$—OH)

5-Aminopentan-1-ol was dissolved in anhydrous methanol and placed in a dry 100 ml container under argon and under anhydrous conditions.

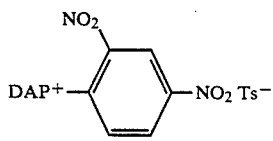

was dissolved in anhydrous methanol and poured dropwise, via a dropping funnel, into the solution of 5-aminopentan-1-ol at 20° C., with stirring. The solution obtained is red and then becomes dark red. Stirring was continued for a further two hours and the methanol was then removed in vacuo, almost to dryness. 250 ml of ether were then added to the residue and a brown precipitate formed; this was separated off by filtration, taken up with methanol and dried.

A single spot was noted in thin layer chromatography on silica gel, using a CHCl$_3$/CH$_3$OH mixture (5%/95%) as the eluent.

Yield 72% - Melting point above 250° C.

NMR D$_2$O/TMPS:

| |
|---|
| δ = 9.65 s |
| δ = 9.3 s |
| δ = 8.23 q |
| δ = 7.49 d |
| δ = 7.18 d |
| δ = 5.11 t |
| δ = 3.67 t |
| δ = 2.32 p |
| δ = 1.60 pp | with δ = 7.49 d and δ = 7.18 d forming an AB system.

EXAMPLE 7: Preparation of the diazapyrene derivative of formula I

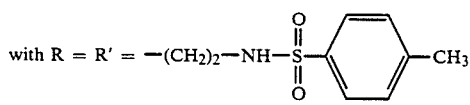

25 mg (1.22·10$^{-4}$ mol) of DAP were dissolved in 5 ml of cold collidine. The following were added to this solution in immediate succession:

48.2 mg (2.44·10$^{-4}$ mol) of tosylaziridine and
38.4 mg (2.44·10$^{-4}$ mol) of collidinium chloride.

The whole mixture was heated from 20° C. to 100° C. over a period of 2 hours, with stirring. The solution changed from dark brown to dark yellow and was decanted and then evaporated to dryness by heating at 50° C.

The product obtained gave a single spot in thin layer chromatography on silica gel (elution with methanol/CH$_2$Cl$_2$ 2%/98%).

Yield: 48%

The NMR spectrum of the product is as follows:

| |
|---|
| δ = 9.5 s |
| δ = 8.4 s |
| δ = 7.8 |
| δ = 7.75 |
| δ = 7.43 |
| δ = 7.39 |
| δ = 3.5 t |
| δ = 3.2 t |
| δ = 2.4 s | with δ = 7.8, 7.75, 7.43, 7.39 forming an AB system.

EXAMPLE 8: Preparation of the diazapyrene derivative of formula I with R = R' = R$_1$Y$^-$

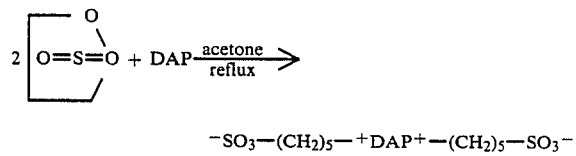

$^-$SO$_3$—(CH$_2$)$_5$—$^+$DAP$^+$—(CH$_2$)$_5$—SO$_3^-$ 25 mg of DAP were partially dissolved in anhydrous acetone (1 ml) and heated to the reflux temperature; propanesultone (45 mg) was added and the mixture was stirred under reflux overnight.

The product obtained gave a single spot in thin layer chromatography on silica gel (eluent: methanol/CH$_3$Cl$_3$ (sic) 10%/90%). The acetone was removed under reduced pressure.

The NMR spectrum in CF$_3$CO$_2^-$D$^+$ gave the following peaks:

| |
|---|
| δ = 8.26 s |
| δ = 6.9 s |
| δ = 3.44 t |
| δ = 1.32 t |
| δ = 0.77 t |

EXAMPLE 9: Preparation of the diazapyrene derivative of formula I

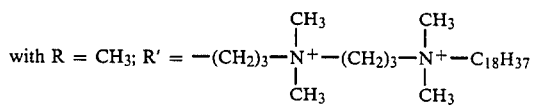

This derivative is prepared by Process C defined above.

DAP$^+$—DNP Ts$^-$ +

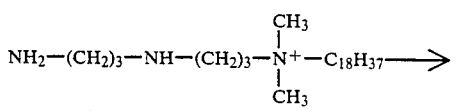

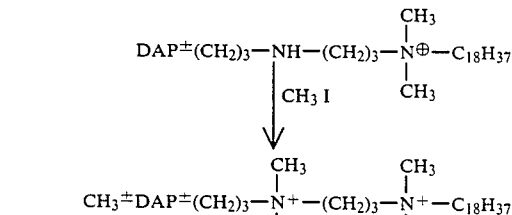

A - Preparation of the compound

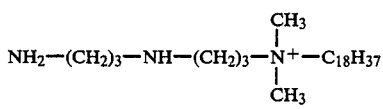

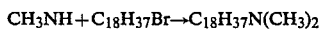      (a)

A solution of 1.6 g of the bromide $C_{18}H_{37}Br$ in 10 ml of ethanol was reacted under reflux with 10 ml of a 33% solution of the amine $(CH_3)_2NH$ in ethanol to give 1.42 g of the tertiary amine $C_{18}H_{37}N(CH_3)_2$.

After the resulting reaction mixture had been reduced to dryness, this amine was purified by extraction with $CHCl_3$ and basic water (containing LiOH). The $CHCl_3$ fraction was filtered and dried.

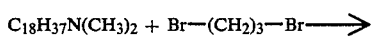      (b)

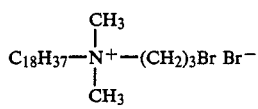

1.4 g of the amine thus obtained were then reacted with 4 ml of the dibromide $Br—(CH_2)_3—Br$ and 10 ml of ethanol, the reaction mixture being refluxed for 20 hours. The solvents were then removed and the residue was dissolved in 5 ml of $CHCl_3$. The solution obtained was poured into ether until precipitation occurred. The pink precipitate formed was filtered off and dried to give 1.8 g of product, which was recrystallized from 40 ml of ethyl acetate. This gave 1.5 g of crystals (yield 98%) of the expected bromide, which has the following $^1H$ NMR spectrum: $\delta$(ppm): 0.875 (t); 1.25 (s); 1.45 (t); 2.39 (p); 3.00 (p); 3.39 (p); 3.45 (t); 3.58 (t); 3.80 (t)

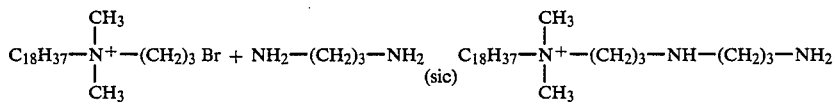      (c)

499 mg of the bromide obtained were reacted with 83.4 μl of propylenediamine, the mixture being heated at 110° C. for 4 h 30 min. The solvent was removed and the residue was isolated by the conventional methods.

The $^1H$ NMR spectrum of the amine obtained is as follows: $\delta$(ppm): 0.78 (t); 1.15 (s); 1.25 (m); 1.6 (t); 1.61 (t); 1.8 (m); 2.55 (t); 2.72 (t); 3.00 (s); 3.15 (t); 3.40 (m)

B. Preparation of the compound of the invention $DAP^+—DNP\ Ts^-$ +

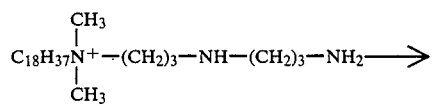

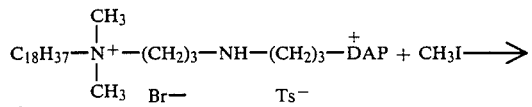

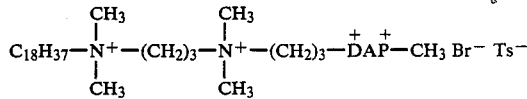

The method of Process C was followed, 43.5 mg ($8.05 \cdot 10^{-5}$ mol) of $DAP^+—DNP\ Ts^-$ being dissolved in 15 ml of methanol, and the solution obtained being added dropwise to a solution of the amine (39.5 mg; $8.05 \cdot 10^{-5}$ mol) in 6 ml of methanol. The slow addition took ½ hour and was followed by stirring for 4 h 30 min under nitrogen, after which the solvent was removed. Ether was then added and a precipitate formed, which was isolated and purified by the conventional methods.

18.6 mg ($2.2 \cdot 10^{-5}$ mol) of the product thus obtained were then reacted with methyl iodide (3 μl; $2.2 \cdot 10^{-4}$ mol) in DMF at 70° C. for 15 hours. The product obtained was passed over an ion exchange column ($Cl^-$) to give the compound of the formula below:

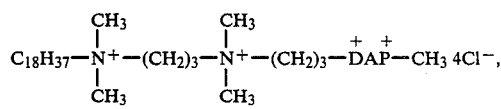

which has a molecular weight of 787 and whose NMR spectrum has the following characteristics:

| | | |
|---|---|---|
| $\delta$ = 0.78 t | $\delta$ = 3.00 s | $\delta$ = 10.44 s |
| $\delta$ = 1.15 s | $\delta$ = 3.24 s | $\delta$ = 10.52 s |
| $\delta$ = 1.25 m | $\delta$ = 3.40 m | |
| $\delta$ = 1.6 t | $\delta$ = 5.05 s | |
| $\delta$ = 1.8 m | $\delta$ = 5.45 t | |
| $\delta$ = 2.55 t | $\delta$ = 9.09 AB system | |
| $\delta$ = 2.72 t | $\delta$ = 10.26 s | |

EXAMPLE 10: Preparation of the diazapyrene derivative of formula I

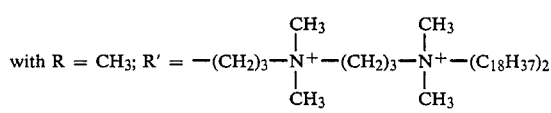

This derivative is also prepared by Process B defined above, $DAP^+—DNP\ Ts^-$ being reacted with the amine of the formula:

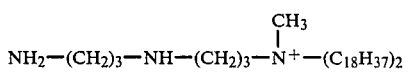

A. Preparation of the amine

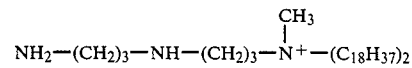

-continued

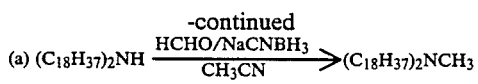

1.5 g of the amine are heated to 80° C. in 20 ml of CH₃CN; 1.1 ml of formaldehyde are added and the solution is cooled. 0.19 g of NaCNBH₃ is then added, after which 1 ml of glacial acetic acid is added slowly over a period of 10 minutes. The solution is subsequently stirred for two hours and a further 2 ml of glacial acetic acid are then added over a period of ½ hour. The solution obtained is poured into ether and extracted 3 times with 20 ml of 1M NaOH and once with 20 ml of brine. The ether phase was dried over K₂CO₃ and filtered and the solvent was removed. 1.39 g of the expected product were obtained.

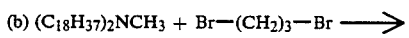

$$(C_{18}H_{37})_2\overset{+}{\underset{CH_3}{N}}-(CH_2)_3-Br\ Br^-$$

The following were stirred under reflux for 14 days: 200 mg of the tertiary amine (obtained in section a) in 3 ml of CH₂Cl₂, 1 ml of the dibromide Br—(CH₂)₃—Br and one crystal of Ki (sic). The solvent was then removed to give 274 mg of the expected product (yield 100%).

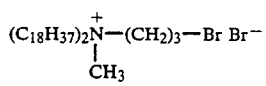

$$(C_{18}H_{37})_2-\overset{CH_3}{\underset{|}{N^+}}-(CH_2)_3-NH-(CH_2)_3-NH_2$$

The procedure described in Example 9.c was followed to give the product characterized by the following ¹H NMR spectrum: δ(ppm): 0.83 (t); 1.20 (s); 1.67 (t); 1.92 (p); 2.69 (t); 2.85 (t); 3.21 (t); 3.31 (t) and 3.57 (t)

B. Preparation of the compound of the invention

The procedure of Example 9 B was repeated to give the following in succession: (1) the compound of the formula:

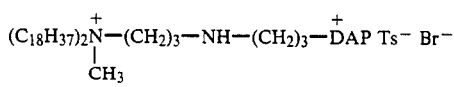

which has the following ¹H NMR spectrum: δ(ppm): 0.94 (t); 1.33 (s); 1.59 (p); 2.29 (s); 2.78 (p); 3.11 (s); 3.20 (t); 5.35 (t); 7.14 (d) and 7.61 (d) (AB system); 8.63 d and 8.76 d (AB system); 9.84 (s) and 10.11 (s)

(2) the compound of the formula:

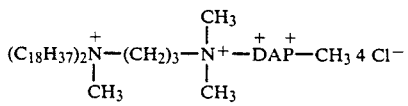

which is characterized by the following ¹H NMR spectrum (DMSO d 6): δ(ppm): 4.32 (s); 4.67 (t); 6.5 (d) and 6.83 (d) AB system); 8.34 (q) and 9.73 (s) AB system); 9.94 (s)

EXAMPLE 11: Preparation of the macrocycle of formula III with p=8

Two solutions were prepared:

Solution I: 2.15 g (0.008 mol) of naphthalene-1,4,5,8-tetracarboxylic anhydride were dissolved in 300 ml of hot DMF (50°-60° C.) and the solution was filtered.

Solution II: 1.15 g (0.008 mol) of 1,8-diaminooctane were dissolved in 200 ml of hot DMF (50°-60° C.), 30 ml of CH₃COOH were then added and the solution was filtered.

250 ml of DMF were placed in a three-necked flask and heated in an oil bath (110°-120° C.). Solutions I and II were added to the DMF simultaneously over a period of 3 to 4 hours. A pale brown precipitate formed during the addition.

After the addition of the two solutions, the reaction mixture was heated for a further hour and the solvent was evaporated off in vacuo.

The solid obtained was suspended in 200 ml of CHCl₃ and the suspension was refluxed for 15 minutes and filtered. This operation was carried out three times in succession. The desired crude product is the one which was insoluble in CHCl₃.

The collected filtrates were washed with 100 ml of a 10% aqueous solution of Na₂CO₃ and 100 ml of brine and dried over Na₂SO₄.

The whole of the organic phase was passed over a silica column and eluted with CH₂Cl₂. The expected product, contaminated with by-products, migrated in the form of a yellowish-pink spot.

The product obtained was suspended in 5 ml of CH₂Cl₂ and the suspension was heated to the reflux temperature, cooled and filtered. The expected product is sparingly soluble in CH₂Cl₂. 0.3 g of practically pure product was obtained by thin layer chromatography on silica gel using a CHCl₃/CH₃OH mixture (99/1) as the eluent (yield: 10%).

The compound obtained (imide) can be crystallized from hot nitrobenzene. It has the following physico-chemical characteristics:

Elemental analysis: C₄₄H₄₀N₄O₈ MW=752.8
calculated: C 70.20 H 5.36 N 7.44
found: C 70.29 H 5.19 N 7.40

¹H NMR spectrum (solvent: CDCl₃) δ(ppm): 8.53 (s, Ar); 4.16 (tr; NCH₂—; J=6.31 Hz); 1.65 (m) and 1.56 (s)

0.26 g (0.002 mol) of AlCl₃ was dissolved in 15 ml of anhydrous THF, and 0.218 g (0.0058 mol) of LiAlH₄ was added. The mixture was stirred and heated to the reflux temperature and the previously obtained imide (0.3 g; 0.0004 mol) was then added in several portions. The resulting mixture was refluxed for 5 hours and then cooled. The excess LiAlH₄ was decomposed by the addition of THF/H₂O (1:1); the solid was filtered off and suspended in 15 ml of THF and the suspension was refluxed for 10 minutes and filtered. This extraction was repeated three times.

The collected organic filtrates were evaporated in vacuo and the crude product was dried. The crude product was then dissolved in 120 ml of CH₂Cl₂, the solution was filtered and the solvent was evaporated off, thereby removing the inorganic compounds. The resulting product was dried in vacuo.

The compound (which is in the form of a yellowish-green gel) can be used in the next step (aromatization with NBS) without further purification.

This compound was purified in the form of its hydrochloride by the following procedure:

The crude product, i.e. the amine of formula VIII, was dissolved in 10 ml of ethanol and 37% aqueous hydrochloric acid up to pH 1, and the solvent was then evaporated off in vacuo. The product (brownish-red oily mixture) was dissolved in a small volume of water and precipitated by the addition of 200 ml of acetone. The precipitate was filtered off and recrystallized from a $CH_3OH/H_2O$ or $CH_3OH/THF$ mixture to give 0.15 g of the amine in the form of its hydrochloride (yield 48%).

Elemental analysis: $C_{44}H_{56}N_4 \cdot 4HCl$ MW=786.8
calculated: C 64.22 H 7.84 N 6.81
found: C 64.50 H 7.92 N 6.27

$^1H$ NMR spectrum (free base, $CDCl_3$): δ(ppm): 7.04 (s, 8H, Ar); 4.00 (s, 16H, $NCH_2Ar$); 2.47 (Tr, 8H, $NCH_2$—$(CH_2)$—(sic)); 1.6 and 1.2 (m, 24H, aliphatic chain)

$^1H$ NMR spectrum (hydrochloride, $D_2O$): δ(ppm): 7.50 (s, Ar); 3.1 (broad); 1.8 (broad); 1.2 (broad); solvent peak at about 4.8 ppm Mass spectrum m/e=640 (for the free base)

The previously obtained amine was dissolved in 80 ml of hot $CH_3COOH$ (about 50° C.) and the solution was filtered and then heated to the reflux temperature. 0.93 g (0.0053 mol) of NBS was added. A reddish-brown solid precipitated instantaneously.

The mixture was refluxed for 30 minutes and the solvent was evaporated off in vacuo. The crude product obtained (brown oil) was mixed with a large volume of water (about 2 liters) and the mixture was heated for 30 minutes at about 80° C. and filtered. The filtrate (pale orange solution) was passed over an Amberlite DG-50H column (in the acid form) and the column was washed thoroughly with water.

The desired product was eliminated from the column with aqueous hydrochloric acid (10%, then 20% and finally 38%) and evaporated in vacuo. It was then dissolved in a small volume of water, precipitated by the addition of acetone, filtered off and dried in vacuo.

Yield: 0.11 g, i.e. 26% based on the imide
Elemental analysis: $C_{44}H_{48}N_4Cl_4$ MW=774.7
$^1H$ NMR spectrum ($D_2O$): δ(ppm): 10.09 (s, Ar); 8.81 (s, Ar); 2.4 (broad, aliphatic chain); 1.5 (broad, aliphatic chain).

What is claimed is:

1. A diazapyrene compound of the formula:

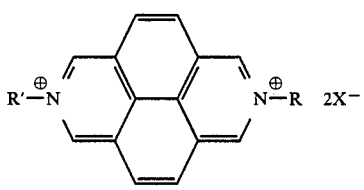

in which R is hydrogen or a lower alkyl group and R' is hydrogen or a substituted alkyl group selected from the group consisting of groups of the formulae —$(CH_2)_n$—SH, —$(CH_2)_n$—OH, and —$(CH_2)_n$—$NH_2$, in which n is from 1 to 10; X is an anion; and R and R' are not both hydrogen at the same time.

2. N-methyl-N'-benzyl-2,7-diazapyrenium dichloride.

3. A diazapyrene compound of the formula:

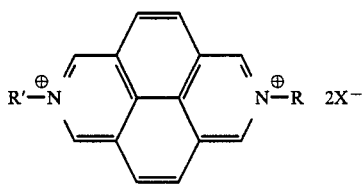

in which the two separate groups R and R' are identical groups and each of the two separate groups is represented by (a) the formula —$R_1Y^-$ in which $R_1$ is —$(CH_2)_3$— and $Y^-$ is the sulfonato ion, $SO_3^-$, or (b) the formula

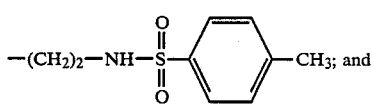

X is an anion.

4. A diazapyrene compound of the formula:

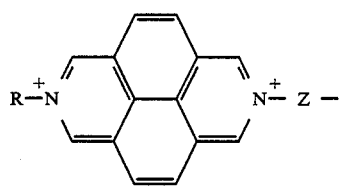

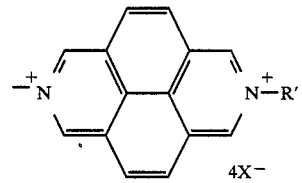

in which:
R and R' are identical or different and each is hydrogen or a lower alkyl group;
X is an anion; and (Z) is selected from the group consisting of divalent radicals of formulae:

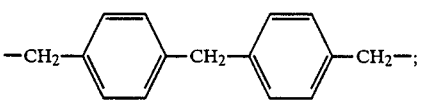

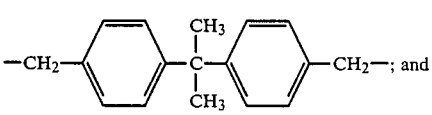

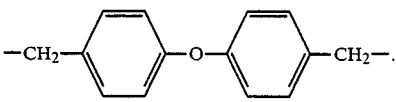

5. A diazapyrene compound of the formula:

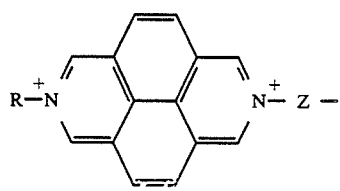
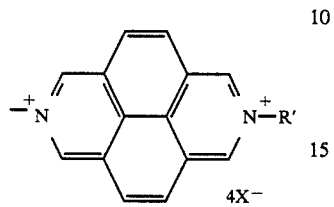
in which:
R and R' are methyl groups, X⁻ is chloride, and (Z) is —CH₂—C₆H₄—CH₂—C₆H₄—CH₂—
6. A compound of the formula
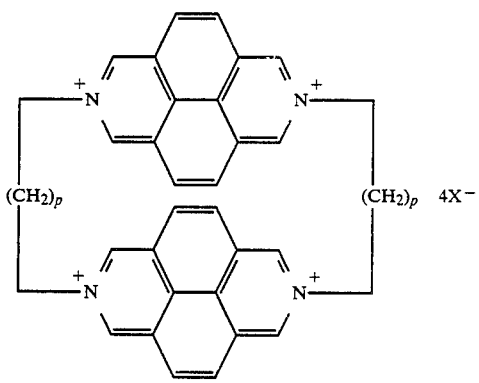
in which p is an integer from 1 to 15 and X is an anion.
7. The compound of claim 6 in which p is equal to 8.
* * * * *